United States Patent [19]

Grothoff

[11] 3,948,817
[45] Apr. 6, 1976

[54] PROPELLING GAS SYSTEM FOR ALCOHOLIC PERFUMED LIQUIDS FOR USE IN AEROSOL DISPENSERS

[76] Inventor: Gisela Grothoff, Nollenlinde 7, 466 Gelsenkirchen-Buer, Germany

[22] Filed: Jan. 23, 1975

[21] Appl. No.: 543,366

Related U.S. Application Data

[63] Continuation of Ser. No. 223,194, Feb. 3, 1972, abandoned.

[52] U.S. Cl. .................................. 252/522; 424/45
[51] Int. Cl.$^2$ ........................................... C11B 9/00
[58] Field of Search ....................... 260/522; 424/45

[56] References Cited
OTHER PUBLICATIONS

Shepherd, Aerosols: Science & Technology, (1961).
Herzka et al., Pressurized Packaging (Aerosols), (1961), pp. 41, 46, & 199.
Herzka, International Encyclopedia of Pressurized Packaging Aerosols, (1966), pp. 558–561.

*Primary Examiner*—C. Davis
*Attorney, Agent, or Firm*—Michael J. Striker

[57] ABSTRACT

For use in aerosol spray dispensers, alcoholic liquid preparations, particularly perfumed liquid preparations, are combined with a liquified propelling gas mutually soluble with said alcoholic preparation, which comprises an aliphatic ether of the formula $CH_3$-O-R in which R is methyl or ethyl.

The combination has better solubility properties in particular in case of low alcohol contents and also in combination with poorly soluble perfuming components and is suited in particular for forming refills in aerosol spray dispensers.

10 Claims, 1 Drawing Figure

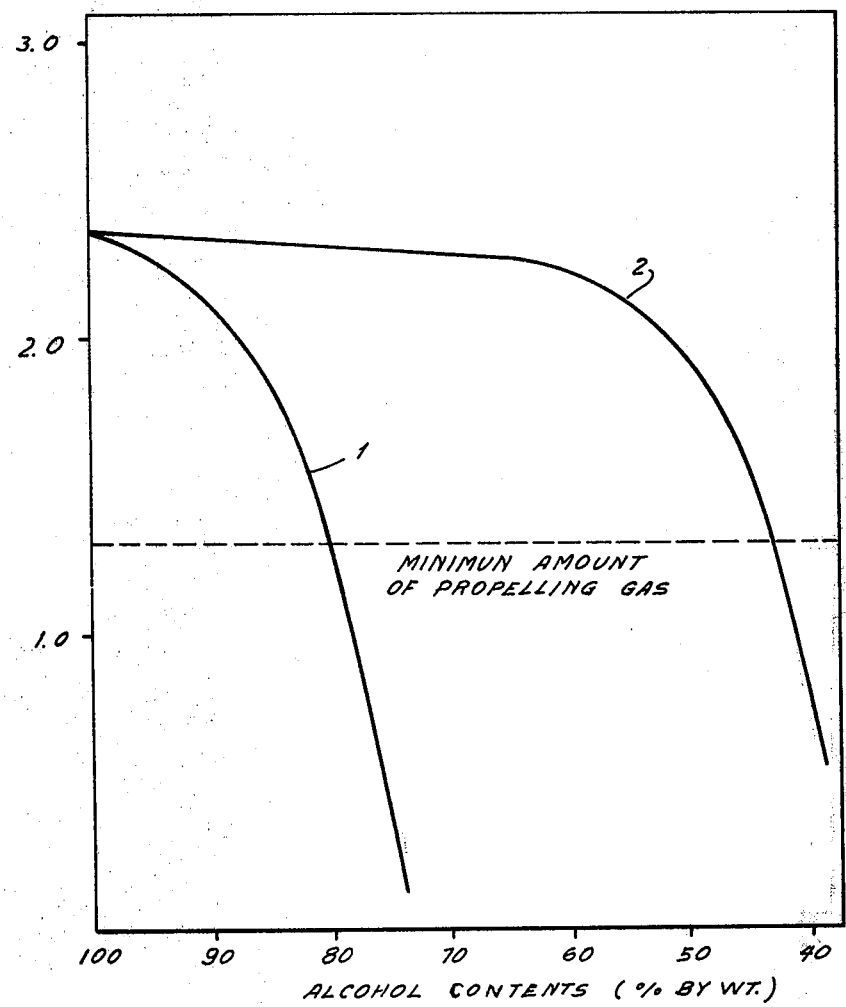

PROPELLING GAS SYSTEM FOR ALCOHOLIC PERFUMED LIQUIDS FOR USE IN AEROSOL DISPENSERS

CROSS REFERENCE TO RELATED APPLICATION

This application is a continuation of my application Ser. No. 233,194, filed Feb. 3, 1972, now abandoned.

BACKGROUND OF THE INVENTION

The invention relates to a propelling gas system for alcohol containing perfuming liquids which are set up in aerosol form under pressure by means of a liquifiable propelling gas and can be used by spray dispensing from the container.

The dispensing and spraying of alcohol-containing fragrancy materials such as perfumes and colognes by means of added liquifiable propelling gases is old. The propelling gases usually comprise aliphatic hydrocarbons such as propane and/or butane as well as fluorinated chlorohydrocarbons such as dichlorodifluoromethane and/or dichlorotetrafluoroethane and mixtures of these materials.

These propelling gases however have various shortcomings for the indicated purposes. Since they have only a low water solubility it is necessary for the perfuming liquids to be dispensed in aerosol form to include a higher percentage alcohol than in containers which are non-pressurized. It is otherwise impossible to dissolve the necessary propelling gas in the perfuming preparation to permit spraying thereof. Frequently phase separation occurs and the further dispensing of the preparation is then impossible. It is also important to note that the solubility of the smelling or scenting components in the perfuming liquid in the above listed propelling gas components is usually below the solubility in alcohol. Therefore flocculations or cystalline precipitations of certain scenting components may occur, sometimes only after a prolonged storage time, which result in clogging up of the valves and thus destroy the usefulness of the dispenser.

These shortcomings can usually be countered by special provisions wherever the perfuming preparation is set up by the manufacturer himself in the aerosol container and thus distributed. These special provisions include the use of a high percentage alcohol for the aerosol dispenser contents.

To use an example the German perfume cologne known under the tradename "Chat Noir Eau de Cologne" uses a 72% alcohol for the normal bottle contents while the same product in aerosol form is used with a 96% concentration alcohol.

Besides, the use in aerosol dispensers is limited to fragrancy combinations which have been tested for this purpose and wherein the mutual solubility of the propelling gases and perfuming liquid has been found to be adequate. All these special provisions and steps of course increase the cost of the final product. Besides they also affect the quality of the product since certain normally not replaceable smelling components must be omitted because of lack of suitability for the aerosol use. This qualitative differentiation appears to the ultimate consumer particularly if he occasionally uses a smelling preparation known to him in an aerosol dispenser instead of a normal bottle container.

All these difficulties are particularly marked if refills are to be composed by the consumer himself by mixing an alcoholic perfuming liquid with a separately added liquifiable propelling gas such as is possible with the type of dispenser disclosed in application No. 97,474 filed by the same applicant on Dec. 8, 1970, now U.S. Pat. No. 3,718,165.

It may be understood that with this type of aerosol refills which are set up by the consumer it is normally not possible to provide for a special composition of the perfuming liquid adapted to aerosol disposal by refillable dispensers. The consumer rather has to rely on the normal bottled perfuming liquid. If these bottle-packed preparations are gasified by the conventional propelling gas the alcohol content of the product which normally is 65 – 80% by weight is usually too low to dissolve the necessary amount of these propellants in the perfuming preparation to permit a satisfactory spraying thereof. Thus the dispenser cannot be completely evacuated. There is furthermore the danger that precipitation and separations of the scenting components occur which may clog up the usually very delicate dispensing valves of the packaging. This difficulty to provide for proper handling of the normal perfume preparations with the conventional propelling gases so far has been an insurmountable obstacle to the introduction and use of refillable aerosol dispensers.

It is therefore an object of the invention to provide for a propelling gas-perfuming liquid combination which has solubility properties to assure a stable and unobjectionable aerosol dispensing even with perfuming liquids of low alcohol contents and also perfuming preparations which contain scenting components which are normally of poor solubility.

More specifically it is an object of the invention to permit dispensing of this type of perfuming preparation by dispensers which may be refilled and gasified by the consumer.

SUMMARY OF THE INVENTION

The invention resides in the combination of a mutually soluble alcoholic liquid preparation, particularly a perfuming preparation, and a liquifiable propelling gas which latter comprises an aliphatic ether of the formula $CH_3-O-R$ in which R is methyl or ethyl. This ether may comprise all of the propelling gas or may be used in the propelling gas in mixture with more conventional saturated aliphatic hydrocarbons of from 3 – 5 carbon atoms, fluorinated chlorocarbon derivatives of methane, ethane or both of these compounds or mixtures of these several conventional propelling gases. In that case at least 15% and preferably in excess of 40% by volume of the propelling gas should consist of the ether.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The drawing is a comparative graphic representation of the solubility properties in alcohol of a conventional propelling gas mixture and a gas mixture of the invention.

DESCRIPTION OF THE INVENTION AND OF SPECIAL EMBODIMENTS

As has already been noted the combinations indicated have a high solubility also in low percentage alcoholic perfuming liquids as compared with conventional propelling gases. This is further apparent from the following synopsis in which the minimum alcohol content is stated at which a mutually unlimited solubility still exists between alcohol and propelling gas:

| | | |
|---|---|---|
| Dimethylether | = 23% | by weight ethylalcohol |
| Methylethylether | = 45% | " |
| Butane | = 97% | " |
| Dichlorodifluoromethane | = 96% | " |
| Dichlorotetrafluoroethane | = 97% | " |

The following examples will further illustrate the invention. These examples show the great superiority of the combinations of the invention regarding their solubility for the various scenting components as compared with conventional propelling gases. The tests which follow have been carried out with vegetable scenting preparations which are in particularly wide use, to wit Bergamot oil and Oak Moss extract (Mousse de Chêne). These two otherwise quite conventional components could not normally be used heretofore for aerosol products.

It is noted that in view of the innumerable scenting components, not all of these or not even the majority could be tested but the same conditions apply and the following examples are considered only as illustrative.

EXAMPLE 1

Bergamot oil was mixed in undiluted form with various propelling gases to provide various concentrations including a final minimum concentration of 0.5% by volume of oil in the propelling gas. The solubility was found to be as follows:

With dimethylether and methylethylether all ratios of mixture down to the above minimum amount resulted in clear solutions which retained their stability also during extended periods of time.

With butane, dichlorodifluoromethane, and dichlorotetrafluoroethane all ratios of mixture resulted in turbid solution and formation of flocculant separations.

EXAMPLE 2

The same test was carried out as in Example 1 but the scenting preparation consisted of oak moss extract.

With dimethylether and methylethylether all ratios of mixture resulted in clear solutions which retained their stability for extended periods of time.

With butane, dichlorodifluoromethane and dichlorotetrafluoroethane the extract remained completely out of solution and the resulting pasty consistency of the extract was not changed with any of the different mixtures.

EXAMPLE 3

1 cc of a 20% solution of an oak moss extract in a 97% by weight ethyl alcohol was mixed with a propelling gas as indicated below until turbidity or precipitation occurred. The amount of propelling gas at which this took place was then determined. The results were as follows:

| | |
|---|---|
| Dimethylether | = infinite solubility, no turbidity occurs |
| Methylethylether | = same results as with dimethylether |
| Butane | = turbidity occurs at 2.5 cc of propelling gas |
| Dichlorodifluoromethane | = turbidity occurs at 2.6 cc |
| Dichlorotetrafluoroethane | = turbidity occurs at 1.9 cc. |

The propelling gases used in the combination of the invention have a faint not unpleasant smell of their own which however is not noticeable when the preparation is sprayed because the scenting components completely obscure and suppress the odor of the propelling gas. Besides the propelling gases are subject to immediate evaporation after application. The toxicity of the combinations of the inventions is likewise extremely low and about comparable to that of the conventional propelling gases. The pressure at 20°C in case of dimethylether is 3.8 atmospheres above atmospheric and in case of methylethylether it is only 0.8 atmosphere above atmospheric. By mixing of the two ethers the desired intermediate pressure can easily be obtained.

The storage loss of material due to diffusion through the outlet valve is not above normal level with the combinations of the inventions and corresponds about to the loss with conventional propelling gases.

It should however be understood that the use of the combinations of the invention would be somewhat limited if the propelling gas was provided in pure form without any other components in a pressure dispenser as this is done with propellant packages for supplying refillable aerosol dispensers with propellant. In this case the strong diffusion properties of the compounds in pure form may cause storage losses which are too high considering a comparatively long storage time such as up to 2 years.

However, in this case according to a special embodiment of the invention the storage losses can be reduced to a normal amount by employing the propelling gases of the invention together with saturated aliphatic hydrocarbons of 3 – 5 carbon atoms and/or fluorinated chlorohydrocarbon derivatives of methane and/or ethane. The ethers of the invention should be used in this case in an amount of at least 15 volume percent and preferably in an amount of in excess of 40 volume percent of the total propelling gas mixture.

EXAMPLE 4

This example illustrates further the packaging loss occurring with pure dimethylether. This loss is compared with a mixture as indicated. Specifically it was found that with a propellant package of pure Dimethylether a storage loss occurred of 12.5 g/year while under otherwise identical conditions a storage loss occurred only of 3.0 g/year in case of a mixture composed as follows:

| | | |
|---|---|---|
| 70% | by volume of | dimethylether |
| 12% | " | dichlorodifluoromethane |
| 18% | " | dichlorotetrafluoroethane. |

It is true that the presence of conventional propelling gases in the propelling gas mixture wll reduce the solubility in low percentage alcohol and also the solubility regarding the scenting components as compared with the pure ethers of the invention. However, the conventional propelling gases are strongly solubilized in these mixtures through the ethers of the invention and it is therefore possible, by suitable selection of the mixing ratio as illustrated by the above example, to still meet the requirements for a useful propelling gas system for aerosol spray dispensers. For instance the above mixture used in Example 4 of 70 volume percent dimethylether, 12 volume percent dichlorodifluoromethane and 18 volume percent of dichlorotetrafluoroethane has an unlimited mutual solubility between propelling gas system and alcohol down to an alcohol content of 62% by weight. This assures that there will be no objection to use in conventional perfuming preparations of even the lowest alcohol contents used in the trade.

It was also found that this mixed propelling gas system when used with the scenting components of Examples 1, 2 and 3 had the same solubility for these scenting components as the pure ethers.

Thus the invention permits to form propelling gas systems which are entirely adequate also for gasifying refills for spray dispensers.

EXAMPLE 5

This example with reference to the drawing further illustrates the improved solubility properties obtainable with the propelling gas system of the invention in case of perfuming liquids which are formed with low percent alcohol contents. This is particularly noticeable when as appears from the drawing the propelling gas systems of the invention are compared with conventional propelling gases.

In the drawing the curve 1 illustrates the solubility properties regarding various alcohol contents of a conventional propelling gas system consisting of 80% by volume of dichlorodifluoromethane and 20% by volume of butane.

Curve 2 illustrates the same properties of a propelling gas system consisting of 70% by volume of dimethylether, 12% by volume of dichlorodifluoromethane and 18% by volume of dichlorotetrafluoroethane which is a preferred embodiment of the present invention.

The curves were obtained on the basis of a refill spray dispenser packaging with a void volume of 8.9 cc. This type of container for each test was filled with 5.0 cc of perfume preparations having varying alcohol contents. It was then closed and gasified under otherwise identical conditions with the two different propelling gas systems. In each case the maximum amount of propelling gas by volume that was dissolved in the perfume preparation was determined.

As appears from the drawing the propelling gas system of the invention results in a substantially constant solubility across a broad range and thus is substantially more suitable than the conventional propelling gas systems. In this case the minimum amount of propelling gas necessary for adequate spray action with both propelling gas systems was considered to be at about 1.3 cc. At this amount of propelling gas which is indicated by the dotted line the minimum alcohol contents for which solubility could be obtained with the conventional propelling gases was 80% by weight of ethyl alcohol. This is inadequate for commercial purposes. On the other hand the propelling gas system of the invention resulted in a minimum solubility at 43% by weight ethyl alcohol. This is adequate even with extremely low percentage alcoholic perfume preparations.

It should also be noted that because of the close chemical relationship between the ether compounds of the invention and the alcohol of the alcoholic perfume preparations precipitations do not occur with the propelling gas systems of the invention except in most unusual cases. This is different with the conventional propelling gas systems where the chemical relation is farther apart and flocculations and precipitations or separations therefor occur quite frequently.

Without further analysis, the foregoing will so fully reveal the gist of the present invention that others can by applying current knowledge readily adapt it for various applications without omitting features that, from the standpoint of prior art, fairly constitute essential characteristics of the generic or specific aspects of this invention and, therefore, such adaptations should and are intended to be comprehended within the meaning and range of equivalence of the following claims.

What is claimed as new and desired to be protected by Letters Patent is set forth in the appended claims:

1. A perfume composition adapted for dispensing in a pressurized aerosol dispenser which consists essentially of a solution in an aqueous ethyl alcohol solvent of conventional perfume ingredients and a propellant comprising a major portion of dimethyl ether or methyl ethyl ether or a mixture of both, the propellant being present in such an amount as to produce an aerosol when the composition is released from a pressurized aerosol dispenser but insufficient to produce precipitation of the perfume ingredients thereof.

2. A composition as defined in claim 1 in which the propellant consists entirely of dimethyl ether, methyl ethyl ether, or a mixture of both.

3. A composition as defined in claim 1 in which the propellant also comprises a conventional propellant of the group consisting of aliphatic hydrocarbons and chlorofluoromethane and chlorofluoroethane gaseous propellants together with at least 15% by volume of dimethyl ether or methyl ethyl ether.

4. A composition as defined in claim 1 in which the propellant comprises at least 40% by volume of dimethyl ether or methyl ethyl ether.

5. A composition as defined in claim 1 in which the propellant consists of dimethyl ether, dichlorodifluoromethane and dichlorotetrafluoroethane in percentages by volume of approximately 70 to 12 to 18, respectively.

6. A composition as defined in claim 1 in which the perfume ingredients include bergamot oil.

7. A composition as defined in claim 6 in which the perfume ingredients include an ethyl alcohol extract of oakmoss.

8. A perfume composition adapted for dispensing in a pressurized aerosol dispenser as defined in claim 1 comprising (a) a perfume component that is poorly soluble in an aqueous ethyl alcohol solvent of low ethyl alcohol content, (b) an aqueous ethyl alcohol solvent of low ethyl alcohol content which by itself is insufficient to dissolve completely the said poorly soluble perfume component, and (c) dimethyl ether, methyl ethyl ether or a mixture of both in such concentration as to dissolve completely the said poorly soluble perfume component and serve as a propellant for the perfume composition.

9. A perfume composition as defined in claim 8 comprising additional conventional propellants of the group consisting of butane, dichlorofluoromethane and dichlorotetrafluoroethane.

10. A composition as defined in claim 1 in which the aqueous ethyl alcohol solvent contains at least 23% by weight of ethyl alcohol when the propellant is solely dimethyl ether, and at least 45% by weight of ethyl alcohol when the propellant is solely methyl ethyl ether, and at least 43% by weight when the propellant is a mixture of 70% by volume of dimethyl ether, 12% by volume of dichlorodifluoromethane and 18% by volume of dichlorotetrafluoroethane.

* * * * *